United States Patent
Devellian (10) Patent No.: US 8,097,015 B2
(45) Date of Patent: Jan. 17, 2012

(54) DEVICE AND METHODS FOR PREVENTING FORMATION OF THROMBI IN THE LEFT ATRIAL APPENDAGE

(75) Inventor: Carol A. Devellian, Topsfield, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 656 days.

(21) Appl. No.: 10/911,980

(22) Filed: Aug. 5, 2004

(65) Prior Publication Data
US 2005/0070952 A1    Mar. 31, 2005

Related U.S. Application Data

(60) Provisional application No. 60/502,702, filed on Sep. 12, 2003.

(51) Int. Cl.
*A61M 29/00* (2006.01)
(52) U.S. Cl. .......... 606/200; 623/1.11; 606/213
(58) Field of Classification Search ........ 623/1.11–1.23, 623/1.1, 1.2, 1.36, 1.41, 1.44, 1.47, 1.49, 623/23.72; 606/200, 1, 151–158, 194, 213, 606/110, 113, 127, 128; 604/500; 128/898, 128/899, 887, 897
See application file for complete search history.

(56) References Cited

U.S. PATENT DOCUMENTS

| 5,192,301 | A | 3/1993 | Kamiya et al. |
| 5,306,234 | A | 4/1994 | Johnson |
| 5,382,261 | A * | 1/1995 | Palmaz ............... 606/158 |
| 5,456,693 | A | 10/1995 | Conston et al. |
| 5,607,444 | A * | 3/1997 | Lam ................. 606/194 |
| 5,823,198 | A | 10/1998 | Jones et al. |
| 5,865,791 | A | 2/1999 | Whayne et al. |
| 5,984,917 | A | 11/1999 | Fleischman et al. |
| 6,007,558 | A | 12/1999 | Ravenscroft et al. |
| 6,096,071 | A * | 8/2000 | Yadav ............... 623/1.15 |
| 6,096,347 | A | 8/2000 | Gedees et al. |
| 6,152,144 | A * | 11/2000 | Lesh et al. ........ 128/898 |
| 6,231,561 | B1 | 5/2001 | Frazier et al. |
| 6,290,674 | B1 | 9/2001 | Roue et al. |

(Continued)

FOREIGN PATENT DOCUMENTS

WO    WO-99/05977    2/1999

(Continued)

OTHER PUBLICATIONS

Oneglia, et al., "Left Atrial Appendage Thrombus as a Source of Peripheral Embolism," Echocardiography: Jml.. of CV Ultrasound & Allied Tech., 2001, vol. 18(5), 389-390.

(Continued)

*Primary Examiner* — Kathleen Sonnett
(74) *Attorney, Agent, or Firm* — DLA Piper LLP (US)

(57) ABSTRACT

The embodiments of the present invention provide a device that modifies the left atrial appendage (LAA) to reduce the likelihood of thrombus formation therein. The device includes a liner that reduces the volume of the LAA and remodels the interior geometry and surfaces of the LAA thereby minimizing the crenellations in the LAA that impede blood flow. According to some embodiments, the device further includes an anchor component. The anchor component helps to expand the liner upon deployment of the device in-vivo and further prevents dislodgement and migration of the device, by ensuring the device is properly seated and completely sealed against the walls and ostium of the LAA.

44 Claims, 8 Drawing Sheets

U.S. PATENT DOCUMENTS

| | | | |
|---|---|---|---|
| 6,328,727 B1 | 12/2001 | Frazier et al. | |
| 6,408,981 B1 | 6/2002 | Smith et al. | |
| 6,419,669 B1 | 7/2002 | Frazier et al. | |
| 6,423,051 B1* | 7/2002 | Kaplan et al. | 604/506 |
| 6,436,088 B2 | 8/2002 | Frazier et al. | |
| 6,447,539 B1 | 9/2002 | Nelson et al. | |
| 6,458,100 B2 | 10/2002 | Roue et al. | |
| 6,485,407 B2 | 11/2002 | Alferness et al. | |
| 6,488,689 B1 | 12/2002 | Kaplan et al. | |
| 6,551,303 B1 | 4/2003 | Van Tassel et al. | |
| 6,561,969 B2 | 5/2003 | Frazier et al. | |
| 6,641,557 B1 | 11/2003 | Frazier et al. | |
| 6,652,555 B1* | 11/2003 | VanTassel et al. | 606/200 |
| 6,652,556 B1 | 11/2003 | VanTassel et al. | |
| 6,666,861 B1 | 12/2003 | Grabek | |
| 6,689,150 B1 | 2/2004 | Van Tassel et al. | |
| 6,712,804 B2 | 3/2004 | Roue et al. | |
| 6,712,836 B1 | 3/2004 | Berg et al. | |
| 6,941,169 B2* | 9/2005 | Pappu | 607/9 |
| 7,128,073 B1* | 10/2006 | van der Burg et al. | 128/887 |
| 7,152,605 B2* | 12/2006 | Khairkhahan et al. | 128/887 |
| 7,278,430 B2* | 10/2007 | Kumar | 128/887 |
| 2001/0025132 A1 | 9/2001 | Alferness et al. | |
| 2001/0034537 A1 | 10/2001 | Shaw et al. | |
| 2001/0039435 A1 | 11/2001 | Roue et al. | |
| 2001/0039436 A1 | 11/2001 | Frazier et al. | |
| 2001/0041914 A1 | 11/2001 | Frazier et al. | |
| 2001/0049492 A1 | 12/2001 | Frazier et al. | |
| 2002/0016626 A1* | 2/2002 | DiMatteo et al. | 623/1.13 |
| 2002/0022860 A1* | 2/2002 | Borillo et al. | 606/200 |
| 2002/0035374 A1 | 3/2002 | Borillo et al. | |
| 2002/0049457 A1 | 4/2002 | Kaplan et al. | |
| 2002/0099390 A1 | 7/2002 | Kaplan et al. | |
| 2002/0103492 A1 | 8/2002 | Kaplan et al. | |
| 2002/0111637 A1 | 8/2002 | Kaplan et al. | |
| 2002/0111647 A1 | 8/2002 | Khairkhahan et al. | |
| 2002/0183823 A1 | 12/2002 | Pappu | |
| 2003/0023262 A1 | 1/2003 | Welch | |
| 2003/0023266 A1* | 1/2003 | Borillo et al. | 606/200 |
| 2003/0057156 A1 | 3/2003 | Peterson et al. | |
| 2003/0073979 A1 | 4/2003 | Naimark et al. | |
| 2003/0083542 A1 | 5/2003 | Alferness et al. | |
| 2003/0120337 A1* | 6/2003 | Van Tassel et al. | 623/1.23 |
| 2003/0181942 A1* | 9/2003 | Sutton et al. | 606/200 |
| 2003/0191526 A1 | 10/2003 | Van Tassel et al. | |
| 2003/0195555 A1 | 10/2003 | Khairkhahan et al. | |
| 2003/0199923 A1 | 10/2003 | Khairkhahan et al. | |
| 2003/0204203 A1 | 10/2003 | Khairkhahan et al. | |
| 2003/0212432 A1 | 11/2003 | Khairkhahan et al. | |
| 2003/0220667 A1 | 11/2003 | van der Burg et al. | |
| 2004/0030335 A1 | 2/2004 | Zenati et al. | |
| 2004/0034366 A1 | 2/2004 | van der Burg et al. | |
| 2004/0044361 A1 | 3/2004 | Franzier et al. | |
| 2004/0049210 A1 | 3/2004 | Van Tassel et al. | |
| 2004/0064138 A1 | 4/2004 | Grabek | |
| 2004/0073241 A1 | 4/2004 | Barry et al. | |
| 2005/0070952 A1* | 3/2005 | Devellian | 606/200 |
| 2005/0222533 A1 | 10/2005 | Chanduszko et al. | |
| 2005/0234540 A1 | 10/2005 | Peavey et al. | |
| 2005/0234543 A1 | 10/2005 | Glaser et al. | |

FOREIGN PATENT DOCUMENTS

| | | |
|---|---|---|
| WO | WO-99/30640 | 6/1999 |
| WO | WO-01/21247 | 3/2001 |
| WO | WO-01/30266 | 5/2001 |
| WO | WO-01/30267 | 5/2001 |
| WO | WO-01/30268 | 5/2001 |
| WO | WO-01/78596 | 10/2001 |
| WO | WO-02/15793 A2 | 2/2002 |
| WO | WO-02/17809 | 3/2002 |
| WO | WO 03/063732 | 8/2003 |

OTHER PUBLICATIONS

Aeba, et al., "Left Atrial Appendage Insertion for Right Ventricular Outflow Tract Reconstruction," Society of Thoracis Surgeons, 2001, vol. 71, pp. 501-506.

Al-Saady, et al., "Left Atrial Appendage: Structure, Function, and Role in Thromboembolism," Heart, 1999, vol. 82, pp. 547-555.

Blackshear, et al., "Appendage Obliteration to Reduce Stroke Cardiac Surgical Patients with Atrial Fibrillation," Society of Thoracic Surgeons, 1996, vol. 61, pp. 755-759.

Crystal, et al., "Left Atrial Appendage Occlusion Study (LAAOS): A Randomized Clinical Trial of Left Atrial Appendage Occlusion During Routine Coronary Artery Bypass Graft Surgery for Long-term Stroke Prevention," American Heart Journal, 2003, vol. 145(1), pp. 174-178.

DiSesa, et al., "Litigation of the Left Atrial Appendage Using an Automatic Surgical Stapler," Society of Thoracic Surgeons, 1988, vol. 46; pp. 652-653.

Kimura, et al., "Effect of Low-Intensity Warfarin Therapy on Left Atrial Thrombus Resolution in Patients with Nonvalvular Atrial Fibrillation," Japanese Circulation Journal, Apr. 2001, vol. 65, pp. 271-274.

Lindsay, B., "Obliteration of the Left Atrial Appendage: A Concept Worth Testing," Society of Thoracic Surgeons, 1996, vol. 61, pp. 515.

Lynch, et al., "Recanalization of the Left Atrial Appendage Demonstrated by Transesophageal Echocardiography," Society of Thoracis Surgeons, 1997, vol. 63, pp. 1774-1775.

Meier, et al., "Contemporary Management of Patent Foramen Ovale," Circulation, 2003, vol. 107, pp. 5-9.

Nakai, et al., "An Endovascular Approach to Cardioembolic Stroke Prevention in Atrial Fibrillation Patents," PACE, 2003, vol. 26, pp. 1604-1606.

Nakai, et al., "Percutaneous Left Atrial Appendage Occlusion (PLAATO) for preventing Cardioembolism," Circulation, 2002, pp. 2217-2222.

Odell, et al., Thoracoscopic Obliteration of the Left Atrial Appendage: Potential for Stroke Reduction? Society of Thoracis Surgeons, 1996, vol. 61, pp. 565-569.

Omran, et al., "Mechanical Occlusion of the Left Atrial Appendage," University of Bonn, pp. S56-S59.

Oneglia, et al., "Left Atrial Appendage Thrombus as a Source of Peripheral Embolism,".

Shirani, et al, "Structural Remodeling of the Left Atrial Appendage in Patients with Chronic Non-Valvular Atrial Fibrillation: Implications for Thrombus Formation, Systemic Embolism, and Assessment by Transesophageal Echocardiography," Cariovascular Pathology, 2000, vol. 9(2), 95-101.

Sievert, et al., Percutaneous Left Atrial Appendage Transcatheter Occlusion to Present Stoke in High-Risk Patients with Atrial Fibrillation, Circulation, 2002, pp. 1887-1889.

Stollberger, et al., "Is Percutaneous Left Atrial Appendage Transcatheter Occlusion an Alternative to Oral Anticoagulation in Patients with Atrial Fibrillation?" Letter to the Editor.

* cited by examiner

DEVICE AND METHODS FOR PREVENTING FORMATION OF THROMBI IN THE LEFT ATRIAL APPENDAGE

CROSS-REFERENCE TO RELATED APPLICATIONS

This application claims benefit to U.S. Provisional Patent Application Ser. No. 60/502,702 filed Sep. 12, 2003.

FIELD OF THE INVENTION

The present invention relates generally to a device that prevents the formation of thrombi in an anatomical appendage, such as the left atrial appendage.

BACKGROUND OF THE INVENTION

Arrhythmias are abnormal heart rhythms. These abnormal heart rhythms may cause the heart to function less effectively. Atrial fibrillation (AF) is the most common abnormal heart rhythm. In AF, the two upper chambers of the heart (i.e., the atria) quiver rather than beat and, consequently, fail to entirely empty of blood. As the blood stagnates on the walls of the atria, it may form thrombi (i.e., clots). Under certain circumstances, these thrombi may re-enter the circulation and travel to the brain, causing a stroke or a transient ischemic attack (TIA).

Figure 1A:
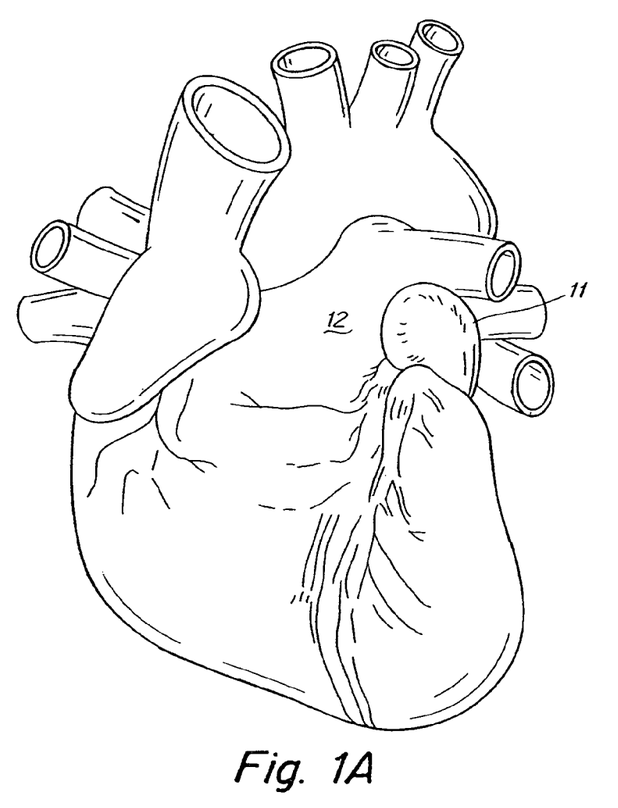
FIGS. 1A and 1B are schematic representations of a human heart, including the LAA.
Figure 1B:
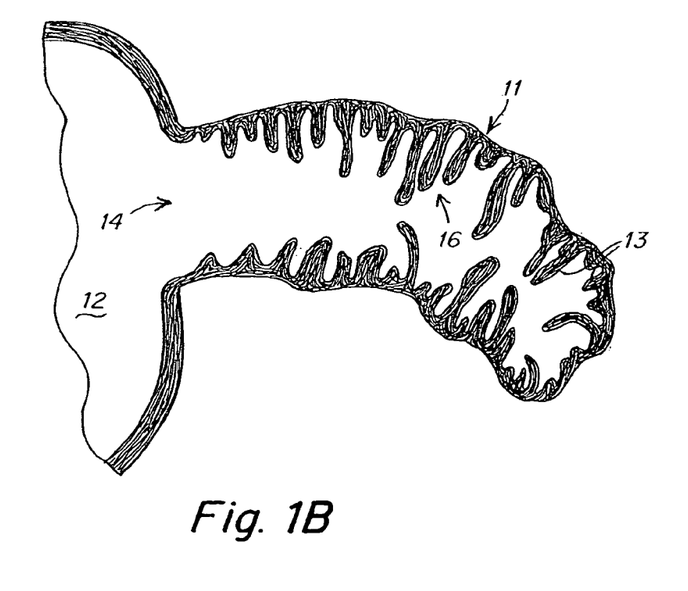

Research has indicated that as many as ninety (90) percent of all thrombi formed during AF originate in the left atrial appendage (LAA). The LAA 11 is a remnant of the original embryonic left atrium that develops during the third week of gestation and, as shown in FIGS. 1A and 1B, is located high on the free wall of the left atrium 12. Long, tubular, and hook-like in structure, the LAA 11 is connected to the left atrium 12 by a narrow junction 14, referred to as the "ostium". The precise physiological function of the LAA remains uncertain: recent reports suggest it may maintain and regulate pressure and volume in the left atrium; modulate the hemodynamic response during states of cardiac stress; mediate thirst in hypovolemia; and/or serve as the site of release of both the peptide hormone atrial natriuretic factor (ANF), which stimulates excretion of sodium and water by the kidneys and regulates blood pressure, and stretch sensitive receptors, which regulate heart rate, diuresis, and natriuresis.

The high rate of thrombus formation in the LAA is believed to be attributable to its physical characteristics; blood easily stagnates, and thereafter clots, in the long, tubular body of the LAA or at its narrow ostium. In marked contrast, the right atrial appendage (RAA), which is a wide, triangular appendage connected to the right atrium by a broad ostium, is infrequently the site of thrombus formation. Thrombus formation in the LAA is further promoted by the numerous tissue folds 13 (i.e., crenellations) on its interior surface 16 (FIG. 1B). These crenellations 13 are particularly hospitable to blood stagnation and clotting, especially when the heart is not functioning at maximum capacity. Thrombi formed in the LAA frequently re-enter the circulation upon conversion of AF to normal rhythm (i.e., cardioversion).

Currently, therapeutic protocols attempt to minimize the likelihood of thrombus formation associated with AF. Blood thinners, such as Warfarin (Coumadin), are, therefore, frequently administered to AF patients. Warfarin administration is, however, complicated by several factors. First, Warfarin is contraindicated for patients suffering from potential bleeding problems or ulcers. Second, Warfarin administration ideally begins approximately four weeks prior to cardioversion and continues for four weeks after cardioversion. This long course of treatment is often compromised due to emergency presentation and/or patient noncompliance.

Certain patient subsets are considered to be at an abnormally high risk of thrombus formation. Such patients include those over seventy-five (75) years of age, as well as those presenting with a history of thromboembolism, significant heart diseases, decreased LAA flow velocity, increased LAA size, spontaneous echogenic contrast, abnormal coagulation, diabetes mellitus, and/or systemic hypertension. For these high-risk patients, prophylactic intervention may be recommended. Current prophylaxes generally fall into three categories: (1) surgical ligation of the LAA as described, for example, in U.S. Pat. Nos. 6,561,969 and 6,488,689; (2) implantation of an LAA occluder sufficient to prevent, or at least minimize, blood flow into the LAA as described, for example, in U.S. Pat. Nos. 6,551,303, 6,152,144, U.S. patent application. No. 2003/0120337, U.S. patent application. No. 2002/0111647, and PCT/US02/23176, and (3) placement of a filter in the LAA ostium to prevent clots formed therein from re-entering the circulatory system as described, for example, in PCT/US03/02395 and PCT/US02/17704.

However, given the uncertain physiological role of the LAA, its obliteration and occlusion remain controversial. Reports have suggested that obliteration of the LAA may decrease atrial compliance and diminish ANF secretion. Furthermore, while properly positioned filter devices prevent migration of thrombi into the circulatory system, they cannot inhibit thrombus formation within the LAA. Consequently, in the event the filter device is dislodged or ineffectively sealed against the LAA ostium, problems plaguing many current filter designs, clots held at the LAA ostium by the filter will be released into the circulation.

Thus, there remains a need in the art for a device capable of preventing thrombus formation in the LAA while maintaining the LAA's function. Such a device must demonstrate excellent dislodgement resistance and, ideally, would be repositionable and retrievable.

SUMMARY OF THE INVENTION

The embodiments of the present invention provide a device that modifies the left atrial appendage (LAA) to reduce the likelihood of thrombus formation therein. The device includes a liner that is a material formed of a flexible, expandable, biocompatible material for covering or coating the inner surfaces of the appendage. The liner may be herein referred to also as a sock portion. According to some embodiments, the device further includes an anchor component.

The liner of the device remodels the interior geometry of the LAA by smoothing its surface and reducing its volume. The liner may be formed of a biologic tissue that is remodeled in-vivo into natural tissue resembling the native endothelium of the LAA. In some embodiments, the remodeled tissue displays functional characteristics similar to those of the native LAA tissue. In particular embodiments, the liner includes a collagenous material derived from the intestinal lining of a warm-blooded mammal, for example, a pig.

According to at least some embodiments, the anchor component of the device is self-expandable and helps to expand the liner upon deployment of the device in the LAA. The anchor component also prevents dislodgement and migration of the device in-vivo by ensuring the device is properly seated and completely sealed against the interior walls and ostium of the LAA.

According to one aspect of the present invention, a device for promoting vascular flow within the left atrial appendage of a heart, includes a liner portion having a proximal end and a distal end, wherein the distal end is expandable and is adapted to be positioned adjacent to a plurality of surfaces of the interior wall of the left atrial appendage such that the liner smoothes the plurality of surfaces of the interior wall; and an anchor component attached to at least a portion of the liner, and adapted for securing the device within the left atrial appendage. The liner can be formed from natural or biologic tissue. The liner can include collagenous material and have a stiffness characteristic that adapts the liner to the surfaces of the interior wall of the LAA. The liner has an appropriate flexibility and resilience which allows for the liner to expand within the LAA. The liner and anchor component are expandable. In an embodiment, the anchor component is self-expandable in-vivo. In an alternate embodiment, the anchor component is expanded with the assistance of a mechanical device, for example a balloon. The liner can further include a lip to seal a portion of the liner in the ostium of the LAA and can have at least one of a plurality of shapes such as, for example, but not limited to, spherical, tubular and conical.

In an embodiment of the present invention, the liner can be or include material promoting cellular in-growth, for example, but not limited to, at least one of synthetic polymers, Teflon-based materials (ePTFE), polyvinyl alcohol (PVA), knitted or woven polyesters, metallic materials, metallic meshes, polyurethanes, and silicone. The anchor component has one of a plurality of shapes which are, for example, but not limited to, a sleeve-like structure, a tubular stent-like structure, a helical coil, a polymeric tube, a conical structure and a metallic mesh. In an embodiment of the present invention, the anchor component is adapted to further include surface characteristics and attachment structures, for example, hooks and surface roughness to augment dislodgement resistance. The anchor component in an embodiment of the present invention can further include a lip at a proximal end to seat and seal at least a portion of the device against the ostium of the LAA. The anchor component is made from material selected from a group including, but not limited to metals, shape memory materials, synthetic polymers, and bioresorbable materials.

In accordance with another aspect of the present invention, a method for promoting drainage of the vascular flow from the left atrial appendage of a heart includes positioning a device having a liner and an anchor component to prevent formation of thrombi. Through a catheter system in a proximal end of the LAA, the proximal end having an ostium; expanding the liner of the device in-vivo in the LAA by using the expandable anchor component wherein the liner extends within the LAA to a distal end of the LAA; and remodeling a plurality of internal surfaces of the internal wall of the LAA using the liner thereby reducing the volume of the LAA and minimizing a plurality of crenellations in the LAA to promote drainage of the vascular flow from the LAA. The liner of the device can include one of a natural and biological tissue. In an embodiment, the liner can include a collagenous material.

In an embodiment, the method includes sealing the ostium of the left atrial appendage by a portion of a lip of the liner. The liner can include material promoting cellular in-growth, for example, at least one of synthetic polymers, Teflon-based materials (ePTFE), polyvinyl alcohol (PVA), knitted or woven polyesters, metallic materials, metallic meshes, polyurethanes, or silicone. In an embodiment, the anchor component can have one of a plurality of shapes, for example, a sleeve-like structure, a tubular stent-like structure, a helical coil, a polymeric tube, a conical structure or a metallic mesh. The anchor component is adapted to further include surface characteristics and attachment structures, for example, but not limited to hooks and surface roughness to augment dislodgement resistance.

In accordance with another aspect of the present invention, a method for manufacturing a device for preventing formation of thrombi in an anatomical appendage includes providing a liner having a proximal end and a distal end; and affixing an anchor component to at least the proximal end of the liner. The liner includes material selected from a group comprising a natural and a biologic tissue. The liner can include material promoting cellular in-growth, for example, but not limited to, at least one of synthetic polymers, Teflon-based materials (ePTFE), polyvinyl alcohol (PVA), knitted or woven polyesters, metallic materials, metallic meshes, polyurethanes, and silicone. The anchor component has one of a plurality of shapes which is, for example, but not limited to, a sleeve-like structure, a tubular stent-like structure, a helical coil, a polymeric tube, a conical structure and a metallic mesh. The anchor component is affixed to a portion of the liner by, for example, one of sewing, gluing, laminating or thermally ligating. The anchor component includes material selected from a group comprising metals, shape memory materials, synthetic polymers, and bioresorbable materials.

In accordance with another aspect of the present invention, a method for deploying in-vivo a device for minimizing the formation of thrombi in the LAA includes inserting a catheter into the right atrium through a lumen in the body, puncturing the septal tissue and placing a guidewire through the septal puncture and into the left atrium; positioning a dilator over the guidewire through the catheter, advancing the dilator and catheter through the septal puncture until they reach the ostium of the LAA, removing the dilator and guidewire and inserting a collapsed device to prevent formation of thrombi in the LAA into the catheter and deploying the device into the ostium of the LAA. The step of deploying includes the anchor component of the device expanding in-vivo into the distal end of the LAA and in turn expanding the liner attached to at least a portion of the anchor component such that the liner is positioned proximate to the surfaces of the interior wall of the LAA. In an embodiment, a dilator/catheter assembly is placed over a guidewire, the dilator/catheter assembly is then advanced through the septal puncture until the assembly reaches the ostium of the LAA.

The foregoing and other objects, features and advantages of the device and methods for preventing formulation of thrombi will be apparent from the following more particular description of preferred embodiments of the device and method as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention provides a device that modifies the LAA to reduce the likelihood of thrombus formation in the LAA during AF and, subsequently, stroke. According to at least some embodiments, this device accomplishes its objective by remodeling the LAA in at least two ways. First, the device reduces the volume of the LAA, thereby minimizing blood stasis during AF. Second, the device smoothes the internal surface 16 of the LAA, thereby obliterating the crenellations that impede blood flow which can lead to blood stagnation and clotting in the LAA. These modifications permit blood to enter and exit the LAA more easily during AF. Thus, the device promotes or enhances the drainage of vascular flow from the LAA. Advantageously, because the device modifies, rather than eliminates, the LAA and potentially maintains LAA function, it overcomes the controversy and potential drawbacks associated with current LAA obliteration or ligation procedures.

In the description herein "distal" refers to the direction away from a catheter insertion location and "proximal" refers to the direction nearest the insertion location.

Figure 2A:
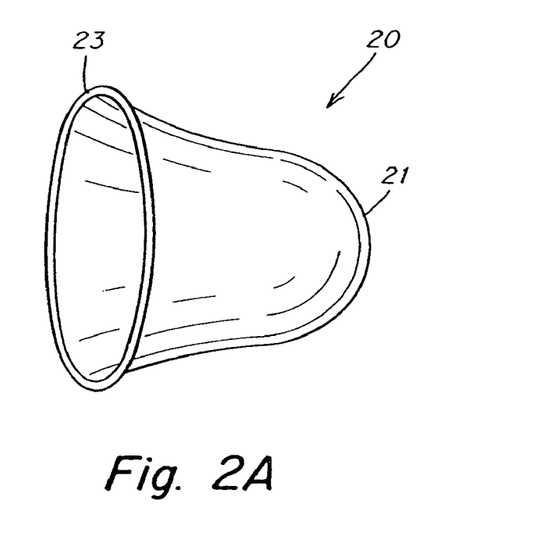
FIG. 2A is a schematic representation of a device according to one embodiment of the present invention.
Figure 2B:
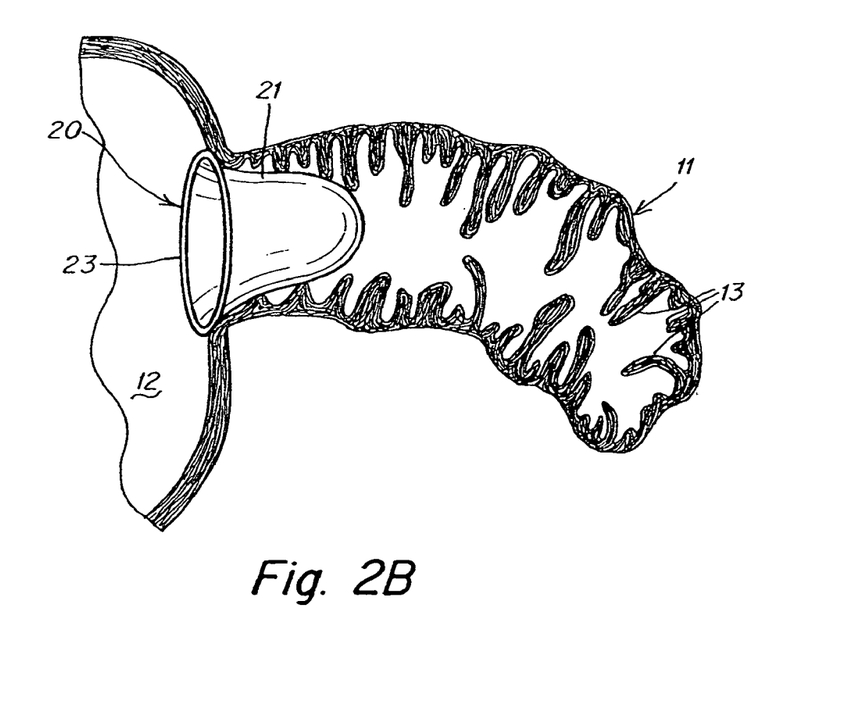
FIG. 2B is a schematic representation of the device of FIG. 2A deployed in the LAA in-vivo.

The device 20 of a preferred embodiment of the present invention includes a liner 21, as shown in FIG. 2A. When deployed in-vivo, the liner or sock component, used interchangeably herein extends into the LAA 11, remodeling its interior geometry and surface (FIG. 2B). According to at least some embodiments, the liner 21 reduces the volume of the LAA, thereby minimizing the access of blood to those areas in the LAA 11 in which it tends to stagnate and clot. In particular embodiments, the liner 21 reduces the depth of the LAA 11 (FIG. 2B).

Figure 4:
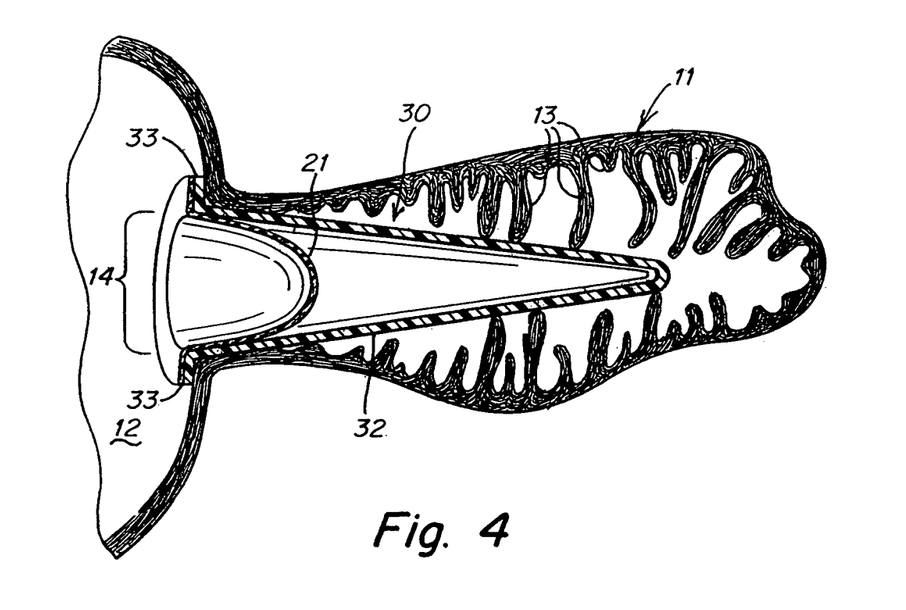
FIG. 4 is a schematic representation of the device of FIG. 3 deployed in the LAA in-vivo.

The liner 21 is generally closed at its distal end and may take any of a variety of shapes depending upon the particular anatomy of the patient's LAA. For example, the sock may be rounded (FIG. 2A), tubular (like a thumb or actual foot sock), or conical. According to at least some embodiments, the shape of the liner 21 includes few, if any, sharp angles. In particular embodiments, and as shown in FIG. 4, the liner 21 is a half sphere. The half sphere design provides a smooth, broad interior surface and promotes drainage of blood from the LAA 11 during AF by, inter alia, reducing the depth of the LAA 11.

In at least some embodiments, the sock 21 is fabricated from a natural or biologic material. Such biologic materials undergo controlled remodeling in-vivo by the patient's own cells. This remodeling occurs as part of the normal healing process through cellular infiltration into the biologic material, over time replacing the biologic material with newly-formed native extracellular matrix (ECM). As part of this healing process, the blood-contacting surface of the liner or sock 21 is covered with endothelial cells, rendering the exposed surface of the sock 21 non-thrombogenic. Often, the remodeled tissue exhibits characteristics similar to that of the native LAA tissue, including distensibility to aid in modulation of left atrial pressure-volume relationships and release of both ANF, which stimulates excretion of sodium and water by the kidneys and regulates blood pressure, and stretch sensitive receptors, which regulate heart rate, diuresis, and natriuresis. The liner material also mimics the material characteristics of the native myocardial tissue, for example, but not limited to, the stiffness and permeability characteristics.

One skilled in the art will, of course, recognize that numerous natural and biologic materials are suitable for use in the liner 21 of the device 20. For example, in at least some embodiments, the sock 21 includes a collagenous material. The collagenous material may be derived from numerous sources, such as the submucosal tissue of a warm-blood vertebrae. In particular embodiments, the collagenous material is derived from the lining of the porcine small intestine. These intestinal collagenous materials are particularly suited for use in the present invention because their non-porous nature provides an "instant seal" upon deployment of the device 20 in the LAA 11, i.e., communication between the blood behind the device 20 and the left atrium 12 ceases as soon as the device 20 is properly deployed in the LAA 11. Further, the in-vivo remodeling of these intestinal collagenous materials does not implicate sloughing of their components, which, correspondingly, reduces the likelihood of adverse embolic events following their implantation. In particular embodiments, the collagenous material(s) may be treated to remove non-collagenous components, for example, without limitation, cells, cellular debris, and extracellular matrix components. These "treated" collagenous materials are notably efficacious matrices for tissue regeneration and remodeling. Tissue derived from the porcine small intestine and subjected to this treatment is referred to as "highly purified (acellular) bioengineered type I collagen derived from porcine submucosa." Other tissue-engineered biomaterials suitable for use in the sock component 21 include reconstituted human collagen, bovine derived products, and bladder intestine.

According to some embodiments of the present invention, the liner 21 may instead be fabricated from a material capable of promoting cellular ingrowth. Such a material encourages the patient's natural cellular remodeling processes discussed previously. Once covered by natural tissue, the foreign material of the device 20 is insulated from the blood flowing through the LAA 11, prolonging its life and improving its dislodgement resistance. As used herein, the term "dislodgement resistance" refers to the ability of a device 20 to resist the tendency of the heart's contractions to separate the device 20 from the LAA 11. Generally, a high dislodgement resistance is desirable. Examples of materials capable of promoting cellular in growth and suitable for use in the embodiment of the present invention include, without limitation, resorbable synthetic polymers, nonresorbable synthetic polymers, such as knitted and woven polyesters, Teflon-based materials (ePTFE), polyvinyl alcohol (PVA), metallic materials, metallic meshes, polyurethanes, silicone, or combinations of the foregoing materials.

The sock component 21 may include a lip 23, as shown in FIG. 2A. Lip 23 properly seats and completely seals the sock component 21 in the ostium of the LAA 11 (FIG. 2B). Lip 23 may be of various shapes and sizes depending upon the application. For example, and as shown in FIGS. 2A and 2B, lip 23 may be circular.

Figure 3:
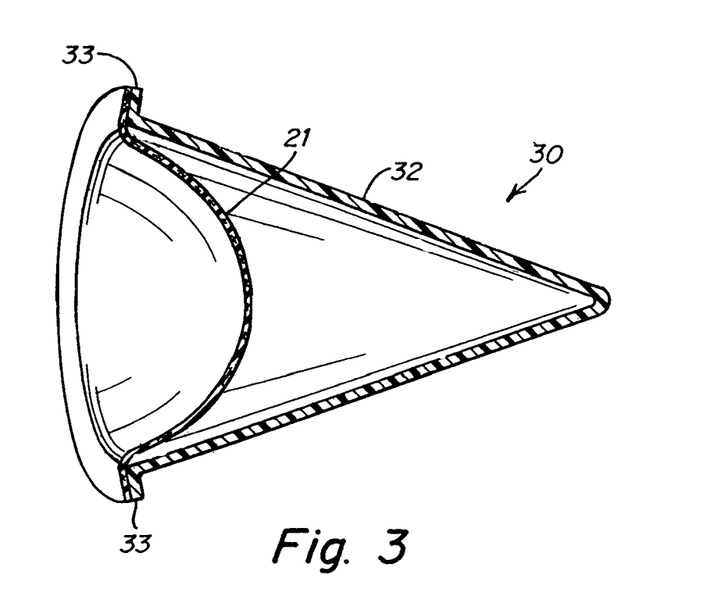
FIG. 3 is a schematic representation of a device according to a further embodiment of the present invention.

According to at least some embodiments of the present invention, the device 20 further includes an anchor component 32 (FIG. 3). The anchor component 32 maintains the liner at its intended delivery site and seals the device to the LAA periphery (FIG. 4). As shown in FIG. 3, the sock component 21 is attached to the anchor 32. The liner 21 and anchor 32 components may be attached by any appropriate method. For example and according to some embodiments, the sock component 21 may be sewn, glued, laminated, or thermally ligated to the anchor 32. One skilled in the art will be capable of identifying other suitable means for attaching the sock component 21 to the anchor component 32 and of determining the precise means of attachment necessary for a given application.

The anchor component 32 of the device 30 according to a preferred embodiment of the present invention is generally self-expandable and, upon deployment of the device 30 in-vivo, simultaneously expands the sock component 21. According to at least some embodiments, the anchor component 32 expands in-vivo to a size greater than that of the LAA 11 and its ostium 14. For example, the anchor component 32 may expand to a size that is ten (10) to twenty (20) percent greater than the LAA ostium 14. In an alternate embodiment, the anchor component is expanded with the assistance of a mechanical device, for example, a balloon.

The expanded anchor component 32 creates a friction between the device 30 and the LAA walls that helps to maintain the device 30 at its intended delivery site. The design of the anchor 32 effectively seals the device against the LAA surface and ostium 14 in-vivo to further prevent dislodgement and migration of the device 30 following deployment (FIG. 4). In at least some embodiments, the anchor 32 may also be designed to facilitate retrieval and/or redeployment of the device. The anchor 32 may be formed of various materials, such as, for example, metals, shape memory materials, or polymers (shape memory, synthetic, or bioresorbable). According to at least some embodiments, the anchor 32 is formed of a bioresorbable material.

Figure 5A:
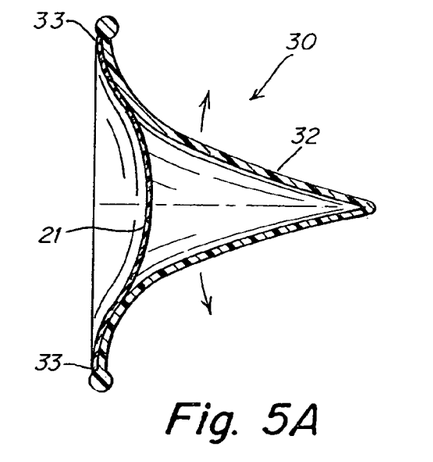
FIGS. 5A-5C are schematic representations of various devices according to still further embodiments of the present invention.
Figure 5B:
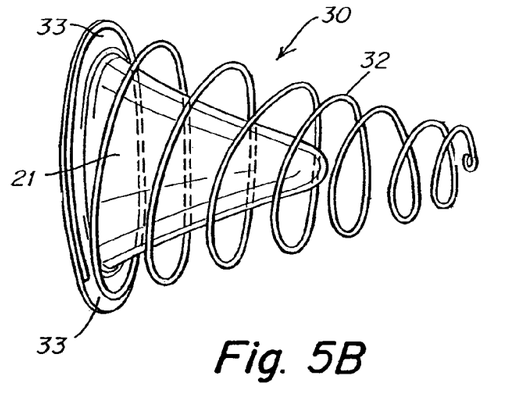
Figure 5C:
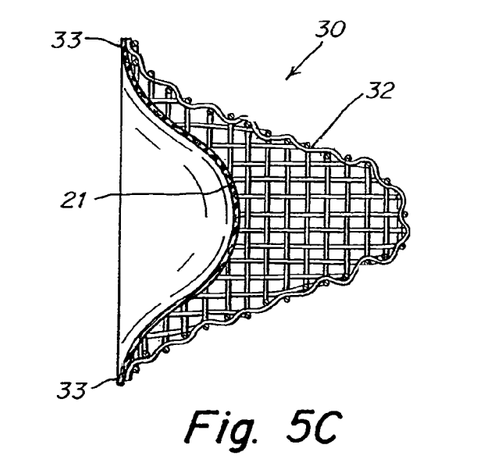

The anchor component 32 may take any of a number of shapes capable of achieving the above-described functions. The anchor 32 may be a sleeve-like structure that expands upon deployment in-vivo to exert radial pressure on the walls of the LAA 11 to hold the device 30 in place (FIG. 5A). According to such an embodiment, the anchor component 32 may be a tubular stent-like structure, a helical coil (FIG. 5B), a polymeric tube, a conical structure (FIG. 3), or a metallic mesh (FIG. 5C). In particular embodiments, the sleeve-like structure includes an implant grade metal, for example, nitinol. The anchor 32 may be further modified to increase the dislodgement resistance of the device 30; for example, the anchor 32 may include hooks and/or its surface may be roughened. According to some embodiments, the anchor 32 is also physically attached to the interior surface of the LAA 11 by a suitable mechanism, such as a suture, weld, glue, or adhesive. For example, the anchor 32 may be attached to the interior surface of the LAA 11 by a glue that is light-activated and cured in situ, once the clinician confirms the device 30 has been properly deployed. One skilled in the art will be capable of determining the precise anchor design and modifications necessary for a particular application.

In at least some embodiments, the anchor component includes a lip 33 at its proximal end. This lip 33 helps to seat and seal the device against the ostium 14 of the LAA 11, thereby ensuring blood is unable to leak into the left atrium 12 from behind the sock component 21 in the LAA 11. As shown in FIGS. 4 and 5, lip 33 may take a variety of shapes and sizes, depending upon the particular application. In other embodiments, the proximal ends of anchor component 32 may be angled such that they engage the inner wall of the LAA 11 and crenellations 13. As the LAA contracts with the heart's rhythm, the angled ends become embedded in the inner wall of the LAA 11 and/or the crenellations 13, such that the device 30 is seated and sealed against the LAA tissue.

Figure 6A:
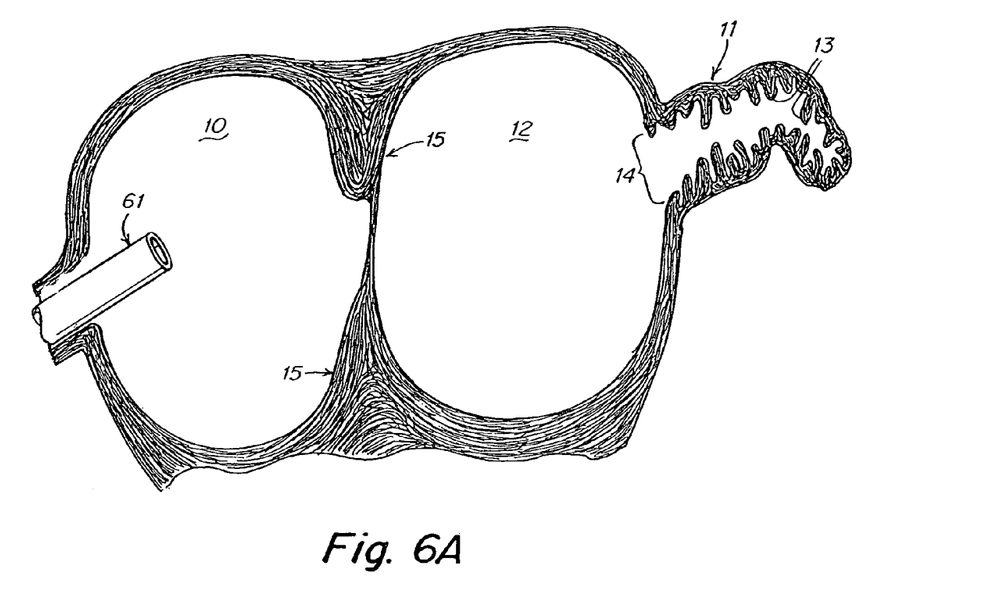
FIGS. 6A-6H are schematic representations of one method of delivering a device to an LAA according to the present invention.
Figure 6B:
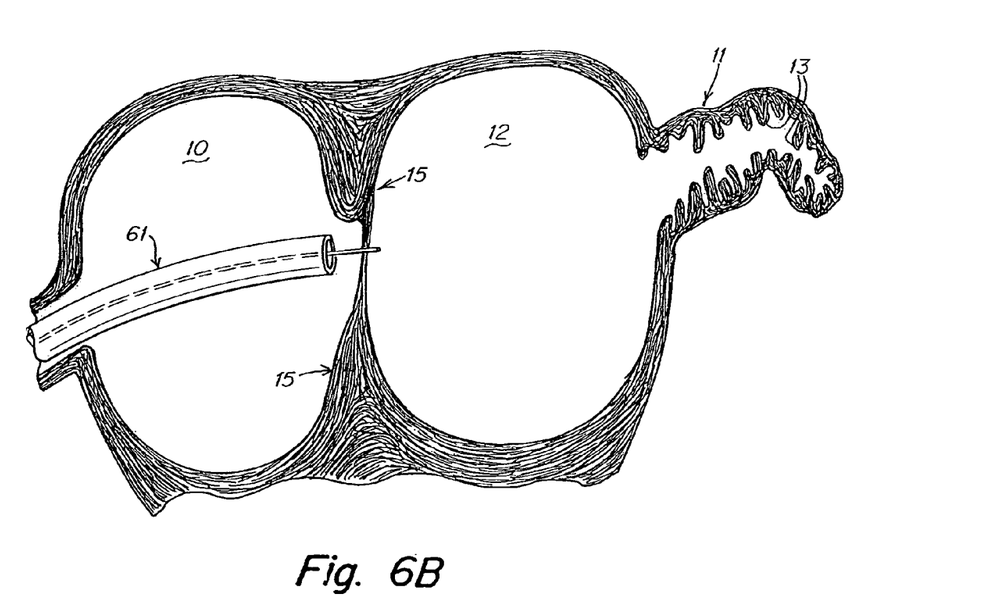
Figure 6C:
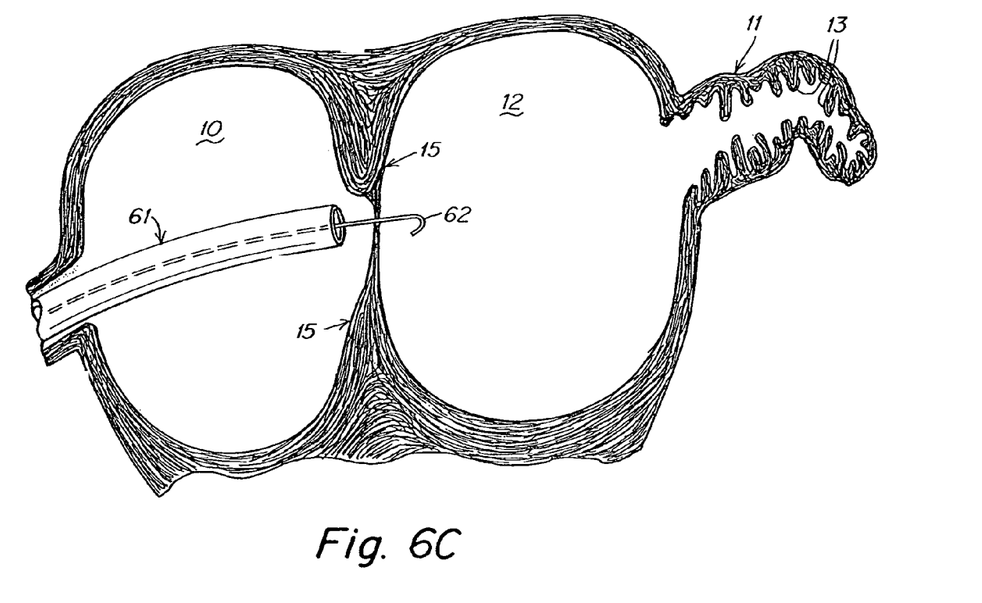
Figure 6D:
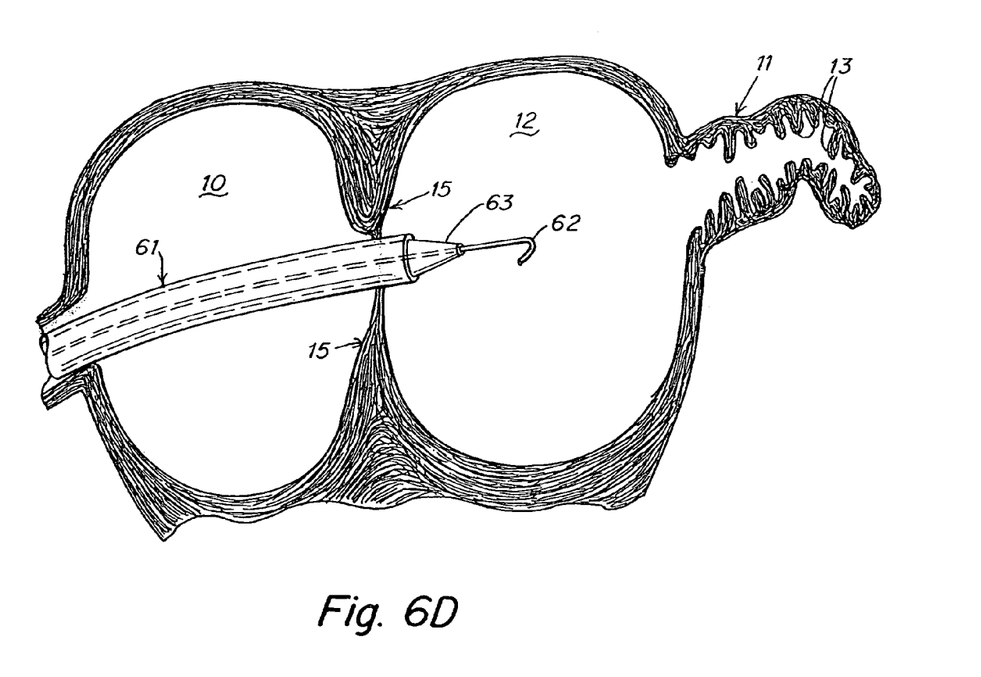
Figure 6E:
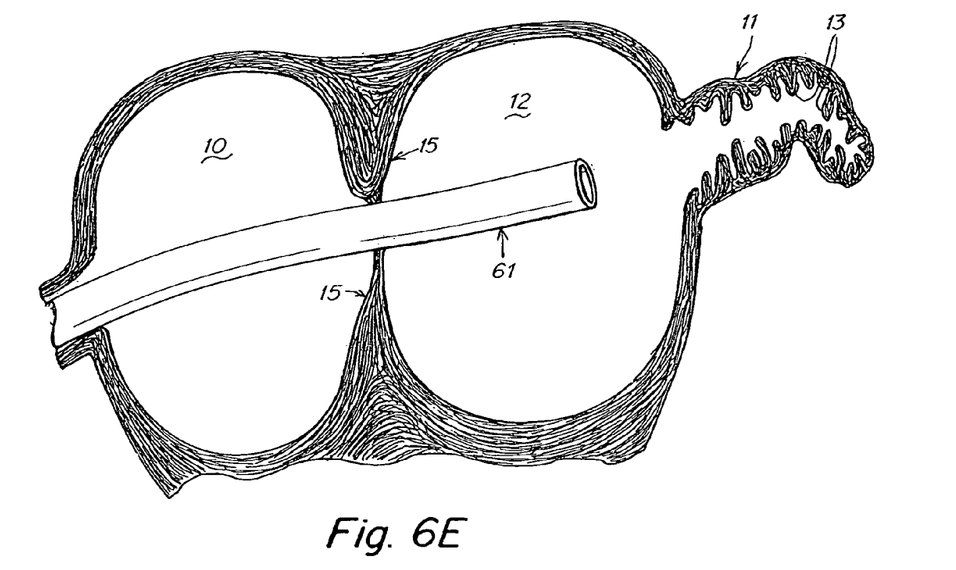
Figure 6F:
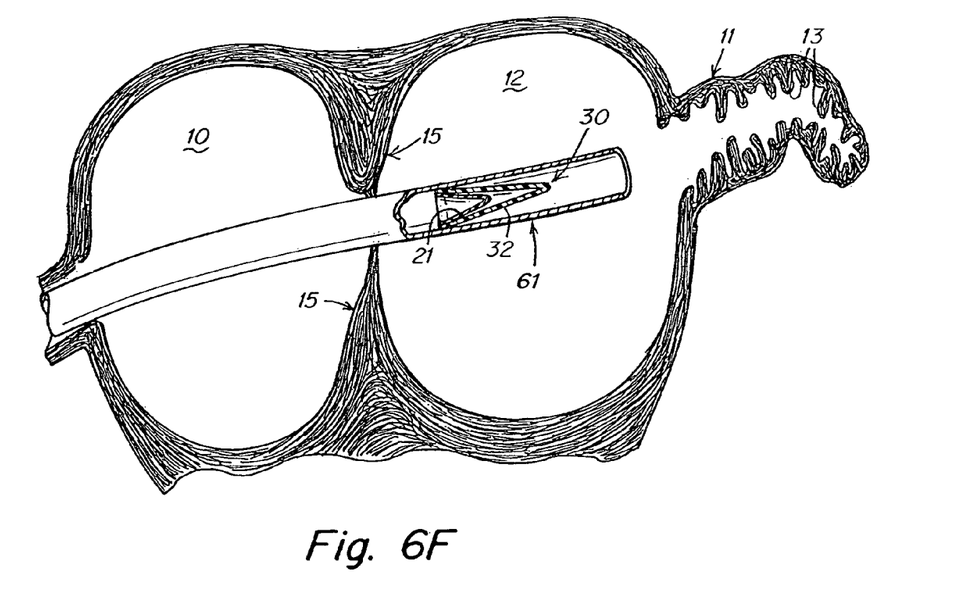
Figure 6G:
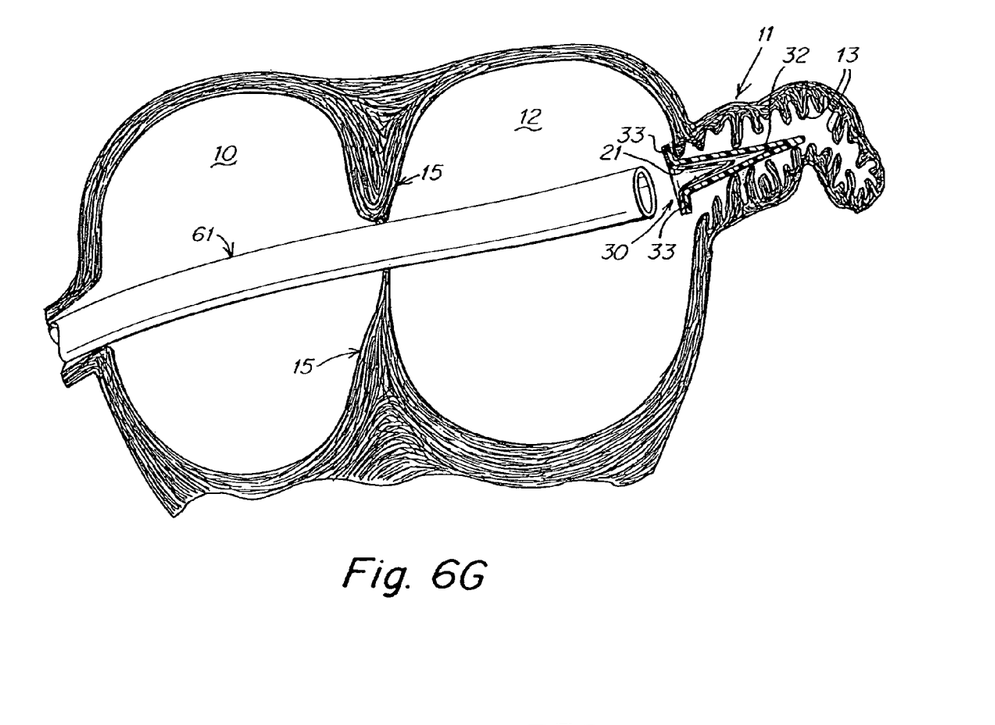
Figure 6H:
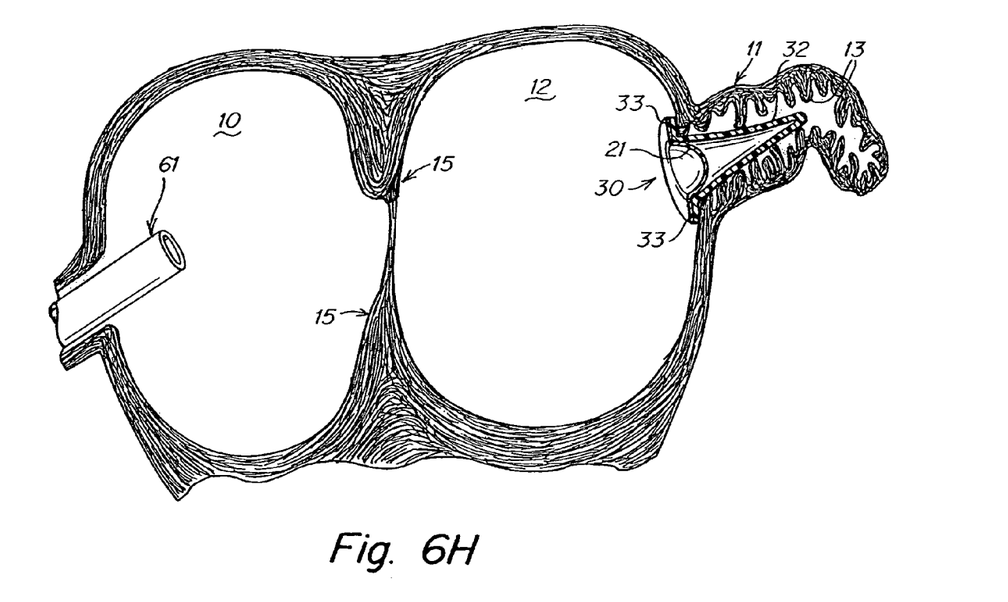

The device 30 according to the present invention may be deployed in-vivo according to any suitable method known to those of skill in the art, only one of which will be described herein (FIGS. 6A-6E). Accessing the heart through the circulatory system, a catheter 61 enters the right atrium 10 (FIG. 6A). The septal tissue 15 is punctured (FIG. 6B), and a guidewire 62 is placed through the puncture and into the left atrium 12 (FIG. 6C). A dilator 63 is placed over the guidewire 62 through catheter 61, and the dilator 63 and catheter 61 are then advanced through the septal puncture (FIG. 6D). In an alternate embodiment, a dilator/catheter assembly is placed over the guidewire and advanced to the ostium of the LAA. Once the catheter 61 has reached the ostium 14 of the LAA 11, the dilator 63 and guidewire 62 are removed, leaving only the catheter 61 in the left atrium (FIG. 6E). The size and shape of the LAA 11 is then observed and measured using echocardiographic techniques and/or fluoroscopy so as to determine the necessary anchor size using the criteria described previously. The selected device 30 is then collapsed, inserted into the catheter 61 (FIG. 6F), and deployed into the ostium 14 of the LAA 11 (FIG. 6G). Following deployment, the anchor component 32 self expands into the LAA 11 and the sock component 21 follows (FIG. 6H). The clinician then confirms the device 30 has been properly placed and an effective seal has been formed between the device 30 and the interior surface and ostium 14 of the LAA 11. If necessary, the clinician may reposition and/or retrieve device 30. Once satisfied with the deployment of the device 30, the catheter 61 is withdrawn from the right atrium 10.

One skilled in the art will recognize that the devices described herein may be used with anti-thrombogenic compounds, including but not limited to heparin (ionic or covalently-bound) and peptides, to reduce thrombogenicity of the device and/or to enhance the cellular in growth of the septal tissue following deployment of the device in-vivo. Similarly, the devices described herein may be used to deliver other drugs or pharmaceutical agents, for example, without limitation, growth factors or antibodies. The anti-thrombogenic compounds and/or pharmaceutical agents may be included in the device in several ways, including impregnation or coating of the sock component and/or anchor component. Further, the devices described herein may include radiopaque fillers for x-ray visualization, cells to promote biocompatibility, echogenic coatings, lubricious coatings, and/or hydrogels.

While the present device has been described with reference to a LAA, one skilled in the art will further recognize that the devices described herein may be used in other anatomical appendages. Further, the steps of any methods or process flow, for example, methods used to deploy the embodiments of the present invention may be taken in sequence other than those described.

Having described preferred embodiments of the invention, it should be apparent that various modifications may be made without departing from the spirit and scope of the invention, which is defined in the claims below.

What is claimed:

1. A device for promoting drainage of the vascular flow from the left atrial appendage (LAA) of a heart, the LAA having an ostium and an interior wall and a distal end, said device comprising:

a liner having a size and shape to conform to an ostium and a portion of the interior wall of an LAA, the liner having a proximal end for placement adjacent to the ostium and a liner distal end, the liner having an opening at the proximal end such that the liner does not substantially obstruct the vascular flow at the ostium, the proximal end including a lip adapted to be disposed along a surface of an atrial wall surrounding the ostium, the lip having a substantially flat portion extending radially outward relative to a central axis of the device, the liner being closed to vascular flow at the liner distal end, the liner distal end adapted to extend toward the distal end of the LAA, and the liner having a portion extending from the lip and toward the liner distal end adapted to extend along and in contact with at least a portion of a surface of the interior wall of the LAA; and an anchor component attached to at least a portion of the liner, the anchor component adapted for securing at least a portion of the device within the LAA, wherein at least a portion of the anchor component is disposed both within the LAA and on an outside of the liner when in a deployed configuration, such that vascular flow within the LAA is promoted.

2. The device of claim 1, wherein the liner comprises one of a natural and biologic tissue.

3. The device of claim 1, wherein the liner comprises collagenous material.

4. The device of claim 3, wherein the collagenous material is treated to remove cellular components.

5. The device of claim 1, wherein the liner is expandable.

6. The device of claim 1, wherein the anchor component is self-expandable.

7. The device of claim 1 wherein the liner has at least one of a plurality of shapes consisting of hemispherical, tubular and conical.

8. The device of claim 1, wherein the liner comprises material promoting cellular in-growth.

9. The device of claim 8, wherein the liner comprises at least one of a synthetic polymer, Teflon-based material (ePTFE), polyvinyl alcohol (PVA), knitted polyester, woven polyester, metallic material, metallic mesh, polyurethane, and silicone.

10. The device of claim 1, wherein the anchor component has one of a plurality of shapes consisting of a sleeve-like structure, a tubular stent-like structure, a helical coil, a polymeric tube, a conical structure and a metallic mesh.

11. The device of claim 1, wherein the anchor component is adapted to further comprise surface characteristics and attachment structures to augment dislodgement resistance.

12. The device of claim 1, wherein the anchor component further comprises a lip at a proximal end to seat and seal at least a portion of the device against the ostium of the LAA.

13. The device of claim 1, wherein the anchor component comprises material selected from a group comprising metals, shape memory materials, synthetic polymers, and bioresorbable materials.

14. The device of claim 1, wherein the anchor component is adapted to exert radial pressure on at least one wall of the LAA.

15. The device of claim 1, wherein the anchor component is adapted to being affixed to at least a portion of an interior surface of the LAA.

16. The device of claim 1, wherein the liner has a material stiffness characteristic that adapts the liner to the surface of the interior wall of the LAA and reduces the prominence of a plurality of surfaces of the interior wall.

17. A method for enhancing vascular flow within the left atrial appendage (LAA) of a heart, said method comprising the steps of:

positioning a device to prevent formation of thrombi through a catheter system in a proximal end of the LAA, the proximal end having an ostium, the device having a liner and an expandable anchor component;

expanding the liner of the device in the LAA by using the expandable anchor component wherein the liner extends from the proximal end of the LAA toward a distal end of the LAA and a portion of the liner between a distal end of the liner and a proximal end of the liner extends along and in contact with at least a portion of a surface of the LAA, wherein the liner proximal end has an opening that permits a substantially unobstructed vascular flow at the ostium and the liner distal end is closed to vascular flow; and remodeling a plurality of internal surfaces of an internal wall of the LAA, including at least internal surfaces between the distal end of the LAA and the proximal end of the LAA, using the liner, thereby reducing the volume of the LAA and reducing the prominence of a plurality of crenellations in the LAA to enhance vascular flow within the LAA, such that vascular flow within the LAA is promoted.

18. The method of claim 17, wherein the liner of the device comprises one of a natural and biological tissue.

19. The method of claim 17, wherein the liner comprises a collagenous material.

20. The method of claim 17, further comprising sealing at least a portion of the ostium of the LAA by a lip of the liner.

21. The method of claim 20, wherein the lip of the liner is adapted to be disposed along a surface of an atrial wall surrounding the ostium and includes a substantially flat portion extending radially outward relative to a central axis of the device.

22. The method of claim 17, wherein the liner comprises material promoting cellular in-growth, including at least one of synthetic polymers, Teflon-based materials (ePTFE), polyvinyl alcohol (PVA), knitted polyesters, woven polyesters, metallic materials, metallic meshes, polyurethanes, and silicone.

23. The method of claim 17, wherein the anchor component has one of a plurality of shapes consisting of a sleeve-like structure, a tubular stent-like structure, a helical coil, a polymeric tube, a conical structure and a metallic mesh.

24. The method of claim 17, wherein the anchor component is adapted to further comprise surface characteristics and attachment structures to augment dislodgement resistance.

25. The method of claim 24, wherein the anchor component comprises at least one of hooks and surface roughness to augment dislodgement resistance.

26. The method of claim 17, wherein the anchor component is self-expanding in vivo.

27. The method of claim 17, wherein the anchor component is expanded with the assistance of a mechanical device.

28. A method for manufacturing a device for preventing formation of thrombi in an anatomical appendage wherein a flow of blood is present, said method comprising the steps of:

providing a liner having a size and shape adapted to extend into the anatomical appendage, having a proximal end and a distal end, wherein the proximal end is open and does not substantially restrict the flow of blood into the anatomical appendage and includes a lip adapted to be disposed along a surface of wall surrounding an ostium of the anatomical appendage, the lip having a substantially flat portion extending radially outward relative to a central axis of the device, and the distal end is closed to the flow of blood, the distal end being dimensioned to extend toward a corresponding appendage distal end, and wherein the liner has a portion extending from the lip and toward the liner distal end adapted to extend along and in contact with at least a portion of a surface of an interior wall of the anatomical appendage, such that vascular flow within the anatomical appendage is promoted; and affixing an anchor component to at least a portion of the proximal end of the liner, wherein the anchor component includes a portion for both extending into the anatomical appendage and being on the outside of the liner.

29. The method of claim 28, wherein the liner comprises material selected from a group comprising a natural and a biologic tissue.

30. The method of claim 28, wherein the liner comprises material promoting cellular in-growth, including at least one of synthetic polymers, Teflon-based materials (ePTFE), polyvinyl alcohol (PVA), knitted polyesters, woven polyesters, metallic materials, metallic meshes, polyurethanes, and silicone.

31. The method of claim 28, wherein the anchor component has one of a plurality of shapes consisting of a sleeve-like structure, a tubular stent-like structure, a helical coil, a polymeric tube, a conical structure and a metallic mesh.

32. The method of claim 28, wherein the anchor component is adapted to further comprise surface characteristics and attachment structures to augment dislodgement resistance.

33. The method of claim 28, wherein the liner has at least one of a plurality of shapes consisting of spherical, tubular and conical.

34. The method of claim 28, wherein the anchor component further comprises a lip at a proximal end to seat and seal at least a portion of the device against an ostium of the appendage.

35. The method of claim 28, wherein the anchor component is affixed to at least a portion of the liner by one of sewing, gluing, laminating and thermally ligating.

36. The method of claim 28, wherein the anchor component comprises material selected from a group consisting of metals, shape memory materials, synthetic polymers, and bioresorbable materials.

37. The method of claim 28, wherein the anatomical appendage is a left atrial appendage in a heart.

38. The method of claim 28, wherein the anchor component is adapted for exerting radial pressure on at least one of a wall of the appendage.

39. A method for deploying in-vivo a device for minimizing the formation of thrombi in a left atrial appendage (LAA) of a heart, the method comprising the steps of:
   inserting a catheter into the right atrium of the heart through a lumen of a body for delivering the device, the catheter including a delivery system;
   puncturing the septal tissue and placing a guidewire through the septal puncture and into the left atrium;
   positioning a dilator over the guidewire through the catheter, advancing the dilator and catheter through the septal puncture until they reach an ostium of the LAA;
   removing the dilator and guidewire;
   inserting the device having a liner and anchor component, wherein the liner is adapted to extend into the LAA toward a distal end of the LAA, the liner having a proximal end for placement adjacent to the ostium and a liner distal end, the liner having an opening at the proximal end such that the liner does not substantially obstruct the vascular flow at the ostium, and being closed to vascular flow at the liner distal end, the device inserted in a collapsed form into the catheter; and
   deploying the device into the ostium of the LAA by expanding the liner of the device to extend at least a portion of the liner between the distal end of the liner and the proximal end of the liner along and in contact with at least a portion of a surface of the LAA, such that the prominence of a plurality of crenellations in the LAA are reduced and vascular flow within the left atrial appendage is promoted.

40. The method of claim 39, further comprising at least one of viewing and measuring the size and shape of the LAA using a scope positioned through the lumen.

41. The method of claim 39, wherein the step of deploying comprises the anchor component of the device expanding in-vivo into the distal end of the LAA and in turn expanding the liner attached at least to a portion of the anchor component wherein the liner is positioned proximate to a plurality of surfaces of interior walls of the LAA.

42. The method of claim 41, wherein the anchor component is self-expanding.

43. The method of claim 41, wherein the anchor component is expanded with the assistance of a mechanical device.

44. The method of claim 39, further comprising sealing at least a portion of the ostium of the LAA by a lip of the liner, wherein the lip of the liner is adapted to be disposed along a surface of an atrial wall surrounding the ostium and includes a substantially flat portion extending radially outward relative to a central axis of the device.

* * * * *